US012594311B2

(12) United States Patent
Zhang et al.

(10) Patent No.: US 12,594,311 B2
(45) Date of Patent: Apr. 7, 2026

(54) *LACTOBACILLUS PLANTARUM* PDG8 AND USE IN TREATING CARDIOVASCULAR DISEASES

(71) Applicant: Pouda Biotech LLC, Radnor, PA (US)

(72) Inventors: Jun Zhang, Xian (CN); Xin Xie, Xian (CN)

(73) Assignee: Pouda Biotech LLC, Radnor, PA (US)

( * ) Notice: Subject to any disclaimer, the term of this patent is extended or adjusted under 35 U.S.C. 154(b) by 350 days.

(21) Appl. No.: 18/323,235

(22) Filed: May 24, 2023

(65) Prior Publication Data

US 2024/0024389 A1      Jan. 25, 2024

Related U.S. Application Data

(60) Provisional application No. 63/347,281, filed on May 31, 2022.

(30) Foreign Application Priority Data

May 26, 2022    (CN) .......................... 202210585567.4

(51) Int. Cl.
| | |
|---|---|
| *A61K 35/747* | (2015.01) |
| *A23L 33/135* | (2016.01) |
| *A61K 35/00* | (2006.01) |
| *A61P 3/04* | (2006.01) |
| *A61P 3/06* | (2006.01) |
| *A61P 9/10* | (2006.01) |
| *C12N 1/20* | (2006.01) |
| *C12N 1/205* | (2026.01) |
| *C12R 1/25* | (2006.01) |

(52) U.S. Cl.
CPC .......... *A61K 35/747* (2013.01); *A23L 33/135* (2016.08); *A61P 3/04* (2018.01); *A61P 3/06* (2018.01); *A61P 9/10* (2018.01); *C12N 1/205* (2021.05); *A61K 2035/115* (2013.01); *C12R 2001/25* (2021.05)

(58) Field of Classification Search
None
See application file for complete search history.

(56)      References Cited

FOREIGN PATENT DOCUMENTS

| | | |
|---|---|---|
| CN | 110714038 A | 1/2020 |
| CN | 111281897 A | 6/2020 |

OTHER PUBLICATIONS

Hassan et al. Appl. Microbiol. Biotechnol. 104: 6337-6350, May 29, 2020.*

Herrero-Fernandez et al., "Immunobiology of Atherosclerosis: A Complete Net of Interactions," *Int. J. Mol. Sci.* 20:5293, 48 pages, 2019.

Lam et al., "Intestinal microbiota determine severity of myocardial infarction in rats," *Faseb J.* 26(4):1727-1735, 2012.

Libby et al., "Progress and challenges in translating the biology of atherosclerosis," *Nature* 473:317-325, May 2011.

Liu et al., "The probiotic role of Lactobacillus plantarum in reducing risks associated with cardiovascular disease," *International Journal of Food Science and Technology* 52:127-136, 2017.

Nordström et al., "Lactiplantibacillus plantarum 299v (LP299V®): three decades of research," *Beneficial Microbes* 12(5):441-465, 2021.

* cited by examiner

*Primary Examiner* — S. Devi

(74) *Attorney, Agent, or Firm* — Seed IP Law Group LLP

(57)      ABSTRACT

Provided are a *Lactobacillus plantarum* strain, *Lactobacillus plantarum* PDG8, and a composition thereof. Also provided are methods using *Lactobacillus plantarum* PDG8 or a composition thereof for treating a cardiovascular disease such as atherosclerosis.

22 Claims, 10 Drawing Sheets

Specification includes a Sequence Listing.

LACTOBACILLUS PLANTARUM PDG8 AND USE IN TREATING CARDIOVASCULAR DISEASES

REFERENCE TO AN ELECTRONIC SEQUENCE LISTING

The contents of the electronic sequence listing (760288_402_SEQUENCE_LISTING.xml; Size: 3,263,391 bytes; and Date of Creation: May 22, 2023) is herein incorporated by reference in its entirety.

TECHNICAL FIELD

The present disclosure relates to a *Lactobacillus plantarum* strain useful in treating a cardiovascular disease, *Lactobacillus plantarum* PDG8. Specifically, the present disclosure relates to a composition, including a pharmaceutical composition, which includes *Lactobacillus plantarum* PDG8 and a culture thereof. The present disclosure also relates to a method of using *Lactobacillus plantarum* PDG8 or a composition containing *Lactobacillus plantarum* PDG8 in treating cardiovascular diseases such as atherosclerosis.

BACKGROUND

Atherosclerosis is a global chronic cardiovascular disease, which is one of the main causes of human disability and even death. The current mainstream strategy for clinical treatment of atherosclerosis is to take statins. Although statins reducing cholesterol synthesis, long-term use can also cause great damage to the liver, and may even increase the risk of heart disease. In more recent proposed treatments, stem cells are used to promote tissue repair and angiogenesis, but the survival rate of stem cells after transplantation is low, the tropism is also relatively poor, and the therapeutic effect is not ideal. The formation of atherosclerotic plaques can also be inhibited by injecting various antibodies and vaccines. However, these treatment options are costly, the operation process is complicated, and the side effects after treatment are difficult to predict and control, and further research is needed to solve them. Accordingly, other treatments for atherosclerosis are needed.

SUMMARY

The present disclosure provides a novel *Lactobacillus plantarum* strain having neurological effects, *Lactobacillus plantarum* PDG8. In addition, the present disclosure provides a composition comprising *Lactobacillus plantarum* PDG8 and a culture thereof. The present disclosure further discloses methods using *Lactobacillus plantarum* PDG8 or a composition containing *Lactobacillus plantarum* PDG8 for treating cardiovascular diseases such as atherosclerosis.

In one aspect, the present disclosure provides an isolated *Lactobacillus plantarum* PDG8 strain deposited at Guangdong Microbial Culture Collection Center (GDMCC) under Accession No. 62261.

In another aspect, the present disclosure provides a composition comprising *Lactobacillus plantarum* PDG8 or a culture thereof and an excipient.

In another aspect, the present disclosure provides a method of treating cardiovascular diseases (e.g., atherosclerosis), comprising administering to a subject in need thereof a therapeutically effective amount of the isolated *Lactobacillus plantarum* PDG8 strain or a composition thereof.

In a related aspect, the present disclosure provides an isolated *Lactobacillus plantarum* PDG8 strain or a composition thereof for use in a method of treating the human or animal body by therapy.

In another related aspect, the present disclosure provides an isolated *Lactobacillus plantarum* PDG8 strain or a composition thereof for use in a method of treating a cardiovascular disease (e.g., atherosclerosis).

BRIEF DESCRIPTION OF THE DRAWINGS

In order to more clearly describe the technical solutions in the embodiments of the present invention, the appended drawings used in embodiments are briefly described below.

FIG. 3A is oil red staining of mouse aortic arch and thoracic aorta. FIG. 3B is the statistical result of the proportion of the lesion area of mouse aortic arch and thoracic aorta.

FIG. 4A is the statistical result of mouse serum total cholesterol, FIG. 4B is the statistical result of mouse serum triglyceride, and FIG. 4C is the statistical result of mouse serum low-density lipoprotein.

FIG. 5A is the statistical result of the level of pro-inflammatory factor IL-6, and FIG. 5B is the statistical result of the level of tumor necrosis factor TNF-α.

DETAILED DESCRIPTION

Figure 1:
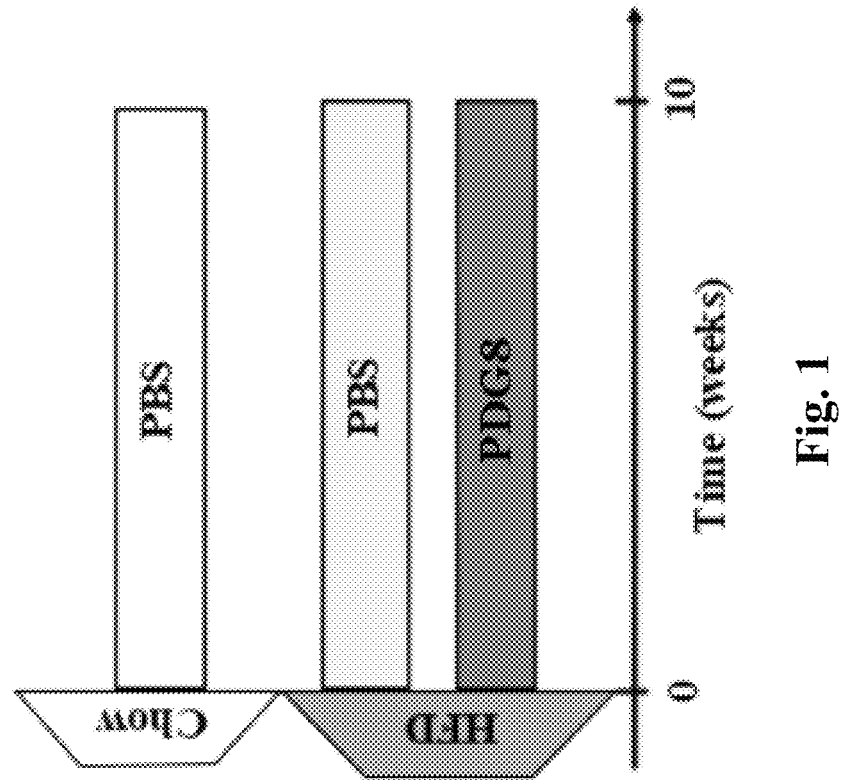
FIG. 1 shows the establishment of the $ApoE^{-/-}$ male mouse model of atherosclerosis as described in Example 1.

Additional aspects and advantages of the present disclosure will become apparent to those skilled in this art from the following detailed description, wherein illustrative aspects of the present disclosure are shown and described. As will be appreciated, the present disclosure is capable of other and different aspects, and its several details are capable of modifications in various respects, all without departing from the disclosure. Accordingly, the descriptions are to be regarded as illustrative in nature, and not as restrictive.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

The present disclosure provides a *Lactobacillus plantarum* strain having neurological effects, *Lactobacillus plantarum* PDG8. In addition, the present disclosure provides a composition, such as a pharmaceutical composition or a nutraceutical composition, which includes *Lactobacillus plantarum* PDG8 and a culture thereof. The present disclosure further discloses methods using *Lactobacillus plantarum* PDG8 or a composition containing *Lactobacillus plantarum* PDG8 for treating cardiovascular diseases (e.g., atherosclerosis).

*Lactobacillus plantarum* PDG8 disclosed herein has one or more of the following characteristics:

a) acid resistance, b) bile resistance, c) no hemolytic activity against red blood cells, d) weak or no antibiotic resistance, e) capable of reducing number or sizes of atherosclerotic plaques when administered to a subject, f) capable of relieving inflammation (e.g., reducing the expression levels of pro-inflammatory factors including IL-6 and INF-$\alpha$ in serum) when administered to a subject, g) capable of reducing blood lipid content (e.g., total cholesterol, triglyceride, and/or low-density lipoprotein cholesterol) when administered to a subject, h) capable of treating a cardiovascular disease (e.g., atherosclerosis) in a subject in need thereof, i) capable of reducing body fat (e.g., abdominal fat) when administered to a subject, j) capable of maintaining or improving the integrity of the intestinal barrier when administered to a subject, k) useful as an active ingredient in a pharmaceutical or nutraceutical composition.

*Lactobacillus plantarum* PDG8

In one aspect, the present disclosure provides a *Lactobacillus plantarum* strain, *Lactobacillus plantarum* PDG8.

As used herein, the term "*Lactobacillus*" refers to a microorganism belonging to the genus of aerobic or facultative anaerobic gram-positive *bacillus* widely distributed in nature. Microorganisms belonging to the genus *Lactobacillus* include *Lactobacillus plantarum*, etc.

The *Lactobacillus plantarum* PDG8 of the present disclosure was obtained by isolation from the fermented vegetables. After isolation and purification, whole genomic sequencing confirmed that the strain is *Lactobacillus plantarum*, belonging to Firmicutes Lactobacillales, Lactiplantibacillus, *Lactobacillus plantarum*. The novel isolated *Lactobacillus plantarum* PDG8 was deposited at Guangdong Microbial Culture Collection Center (GDMCC), Institute of Microbiology, Guangdong Academy of Sciences, No. 59 Building, No. 100 Xianliezhong Road, Yuexiu District, Guangzhou 510075, China, under Accession No. 62261 on Mar. 4, 2022.

The term "isolated" refers to the state of a substance or microorganism separating from its naturally occurring environment. In certain embodiment, at least 50%, such as at least 60%, 70%, 80%, 90%, 95%, 97%, 98%, or 99%, of the materials in the naturally occurring environment other than the substance or microorganism of interest have been removed to generate an isolated substance or microorganism. In certain embodiments, an isolated substance or microorganism is at least 50%, such as at least 60%, 70%, 80%, 90%, 95%, 97%, 98%, or 99% pure. In other words, at least 50%, such as at least 60%, 70%, 80%, 90%, 95%, 97%, 98%, or 99% (by weight) of the isolated substance or microorganism is the substance or microorganism of interest.

The invention further provides a mutant, a variant, and/or a progeny of the deposited *Lactobacillus plantarum* PDG8 strain.

As used herein, the term "mutant" refers to any bacterium resulting from modification of the parent (i.e., deposited) strain. For example, a mutant may be a bacterium resulting from genetically modifying the deposited strain.

As used herein, the term "variant" refers to a naturally occurring bacterium derived from the parent (i.e., deposited)

strain. For example, a variant may be a bacterium resulting from adaption to particular cell culture conditions.

As used herein, the term "progeny" means any bacterium resulting from the reproduction or multiplication of the deposited strain. Therefore, "progeny" means any direct descendant of the deposited strain. As such, the progeny strain may itself be identified as the same strain as the parent (i.e., deposited) strain. It will be apparent to one skilled in the art that due to the process of asexual reproduction, a progeny strain will be genetically virtually identical to the parent strain. Accordingly, in one embodiment, the progeny may be genetically identical to the parent strain and may be considered to be a "clone" of the parent strain. Alternatively, the progeny may be substantially genetically identical to the parent strain.

The mutant, variant or progeny may have at least 90, 95, 98, 99, 99.5 or 99.9% sequence identity over the entire length of the bacterial genome with their parent strain. Furthermore, the mutant, variant or progeny will retain the same phenotype as the deposited parent strain.

As used herein, "identical" or "identity" refers to the similarity between a DNA, RNA, nucleotide, amino acid, or protein sequence to another DNA, RNA, nucleotide, amino acid, or protein sequence. Identity can be expressed in terms of a percentage of sequence identity of a first sequence to a second sequence. Percent (%) sequence identity with respect to a reference DNA sequence can be the percentage of DNA nucleotides in a candidate sequence that are identical with the DNA nucleotides in the reference DNA sequence after aligning the sequences. Percent (%) sequence identity with respect to a reference amino acid sequence can be the percentage of amino acid residues in a candidate sequence that are identical with the amino acid residues in the reference amino acid sequence after aligning the sequences and introducing gaps, if necessary, to achieve the maximum percent sequence identity, and not considering any conservative substitutions as part of the sequence identity. The algorithm used herein for determining percent sequence identity is the BLAST 2.0 algorithm, as described in Altschul et al. "Gapped BLAST and PSI-BLAST: a new generation of protein database search programs," Nucleic Acids Res. 2007, 25, 3389-3402, with the parameters set to default values.

As shown in the Examples below, the *Lactobacillus plantarum* PDG8 is capable of reducing accumulation of fat (e.g., abdominal fat), formation, number and/or sizes of atherosclerotic plaques, amount of blood lipid (e.g., total cholesterol, triglyceride and low-density lipoprotein cholesterol), and expression of pro-inflammatory factors (e.g., TNF-$\alpha$, IL-6) as well as improving the intestinal barrier.

In some embodiments, the *Lactobacillus plantarum* PDG8 may cause fewer side effects or less intense side effects in a patient than a conventional drug for treating a cardiovascular disease (e.g., atherosclerosis), such as a statin. Side effects include headache, dizziness, feeling sick, unusually tired or physically weak, digestive system problems, muscle pain, sleep problems, low blood platelet count, or the like.

In some embodiments, the *Lactobacillus plantarum* PDG8 may be able to colonize the intestine of a patient, and may have resistance to acid and bile salts.

As used herein, the term "acid resistance" refers to the property of withstanding high acidity. If probiotics are acid-resistant, they can be prevented from being degraded or damaged even when exposed to strong acidic conditions in the stomach, by consumption through oral administration.

As used herein, the term "bile resistance" refers to the resistance to digestive enzymes in bile. Bile is made in the liver and stored in the gallbladder, and is a weak alkaline greenish-brown liquid that helps the digestion of fat in the duodenum of the small intestine, and contains various enzymes that help digestion and absorption by emulsifying fat. Bile is one of the major causes of reducing the effect of probiotic administration as it acts on probiotics ingested through oral administration.

The *Lactobacillus plantarum* PDG8 of the present disclosure may not exhibit a hemolytic activity against red blood cells. Hemolysis refers to the destruction of red blood cells and the release of hemoglobin to the surrounding area, and is an action by which the red blood cells are hemolyzed by enzymes produced from harmful bacteria in vivo. Therefore, the *Lactobacillus plantarum* PDG8 is recognized as a stable microorganism that does not cause hemolysis in the blood vessels even if it is administered in vivo.

In addition, the *Lactobacillus plantarum* PDG8 of the present disclosure may have a weak resistance or no resistance to antibiotics. No drug resistant genes were identified in the genome of *Lactobacillus plantarum* PDG8 using AMRFinderPlus, NCBI. Accordingly, when the *Lactobacillus plantarum* PDG8 is used in pharmaceuticals, health functional foods, feed additives, etc., it has little or no resistance to antibiotics, and thus, the probability of causing related pharmacological effects or environmental problems is low.

In some embodiments, the *Lactobacillus plantarum* PDG8 bacteria may be modified using recombinant techniques to contain an antibiotic susceptibility gene or other gene that facilitates destruction of the bacteria after introduction into a patient.

In more specific embodiments, the *Lactobacillus plantarum* PDG8 may be provided as a probiotic.

In order to stably maintain the *Lactobacillus plantarum* PDG8 of the present disclosure for a long period of time, the strain may be stored by dissolving the cells in a storage solution prepared by mixing a certain amount of glycerol in water at −70° C., or may be freeze-dried by for example suspending the cells in sterilized 10% skim milk, but methods of maintaining the strain are not limited thereto.
Compositions Containing *Lactobacillus plantarum* PDG8

In another aspect of the present disclosure, there is provided a composition (e.g., a pharmaceutical composition or a nutraceutical composition) including the *Lactobacillus plantarum* PDG8 bacteria, a culture thereof, a concentrate thereof, or a dried form thereof and optionally an excipient.

In certain embodiments, the composition may comprise, consist essentially of, or consist of isolated *Lactobacillus plantarum* PDG8 bacteria. In other embodiments, the composition may be in a formulation for administration to a patient. In certain embodiments, the composition and/or the excipient is not naturally occurring.

The term "excipient" refers to an inactive substance that serves as the vehicle, carrier or medium for an active substance (e.g., *Lactobacillus plantarum* PDG8 bacteria or culture thereof). An excipient may be included in a composition for the purpose of long-term stabilization, bulking up solid formulations that contain potent active ingredients in small amounts, or to confer a therapeutic enhancement on the active ingredient in the final dosage form, such as facilitating drug absorption, reducing viscosity, or enhancing solubility. Excipients can also be useful in the manufacturing process, to aid in the handling of the active substance concerns such as by facilitating powder flowability or non-stick properties, in addition to aiding in vitro stability such as prevention of denaturation or aggregation over the expected shelf life.

Exemplary excipients including cryoprotectants (e.g., glycerol, trehalose, maltodextrin, skim milk powder, and starch), bulking agents, fillers, diluents, anti-adherents (e.g., magnesium stearate), binders (e.g., saccharides including sucrose, lactose, starches, cellulose, microcrystalline cellulose, hydroxypropyl cellulose, xylitol, sorbitol, or mannitol; proteins including gelatin; and synthetic polymers including polyvinylpyrrolidone (PVP) and polyethylene glycol (PEG)), coatings (e.g., hydroxypropyl methylcellulose, fatty acids, waxes, shellac, and plant fibers), disintegrants (e.g., crosslinked polymers including crosslinked polyvinylpyrrolidone, crosslinked sodium caboxymethyl cellulose, and sodium starch glycolate), flavoring agents (e.g., fruit extract), glidants (e.g., silica gel, fumed silica, talc and magnesium carbonate), lubricants (e.g., talc, silica, fats), preservatives (e.g., antioxidants like vitamin A, vitamin E, vitamin C, retinyl palmitate and selenium; amino acids cysteine and methionine; citric acid and sodium citrate; and synthetic preservatives like the parabens (e.g., methyl paraben and propyl paraben), sorbents, sweeteners, and vehicles (e.g., dimethyl suloxide) for liquid and gel formulations.

In some embodiments, the composition is in the form of a liquid, a suspension, a dried (e.g., lyophilized) powder, a tablet, a capsule, a suppository, or an enema fluid, or a frozen liquid, suspension, or enema fluid. Dried compositions may be produced by air drying, natural drying, spray drying, freeze drying, lyophilization, and any combinations thereof. Compositions in the freeze dried state may include a protectant, such as a cryoprotectant, which may include ethylene glycol, dimethyl sulfoxide (DMSO), glycerol, and any combinations thereof. Such compositions may be reconstituted with a solution, such as a buffer, prior to oral, nasogastrical, or rectal administration.

In a liquid or suspension composition, the concentration of *Lactobacillus plantarum* PDG8 bacteria may be $10^3$ CFU/mL to $10^8$ CFU/mL, $10^4$ CFU/mL to $10^8$ CFU/mL, $10^5$ CFU/mL to $10^8$ CFU/mL, $10^6$ CFU/mL to $10^8$ CFU/mL, $10^3$ CFU/mL to $10^7$ CFU/mL, $10^4$ CFU/mL to $10^7$ CFU/mL, $10^5$ CFU/mL to $10^7$ CFU/mL, $10^6$ CFU/mL to $10^7$ CFU/mL, but is not limited thereto. In a solid composition, the amount of *Lactobacillus plantarum* PDG8 bacteria may be $10^5$ CFU/g to $10^{13}$ CFU/g, $10^6$ CFU/g to $10^{13}$ CFU/g, $10^7$ CFU/g to $10^{13}$ CFU/g, $10^8$ CFU/g to $10^{13}$ CFU/g, $10^5$ CFU/g to $10^{12}$ CFU/g, $10^6$ CFU/g to $10^{12}$ CFU/g, $10^7$ CFU/g to $10^{12}$ CFU/g, $10^8$ CFU/g to $10^{12}$ CFU/g, $10^5$ CFU/g to $10^{11}$ CFU/g, $10^6$ CFU/g to $10^{11}$ CFU/g, $10^7$ CFU/g to $10^{11}$ CFU/g, $10^8$ CFU/g to $10^{11}$ CFU/g, $10^5$ CFU/g to $10^{10}$ CFU/g, $10^6$ CFU/g to $10^{10}$ CFU/g, $10^7$ CFU/g to $10^{10}$ CFU/g, $10^8$ CFU/g to $10^{10}$ CFU/g, $10^5$ CFU/g to $10^9$ CFU/g, $10^6$ CFU/g to $10^9$ CFU/g, $10^7$ CFU/g to $10^9$ CFU/g, $10^5$ CFU/g to $10^8$ CFU/g, or $10^6$ CFU/g to $10^8$ CFU/g by weight of the composition.

In certain embodiments, the composition is provided in unit dosage form. The composition may comprise *Lactobacillus plantarum* PDG8 bacteria in an amount ranging $10^5$ CFU to $10^{13}$ CFU, $10^6$ CFU to $10^{13}$ CFU, $10^7$ CFU to $10^{13}$ CFU, $10^8$ CFU to $10^{13}$ CFU, $10^5$ CFU to $10^{12}$ CFU, $10^6$ CFU to $10^{12}$ CFU, $10^7$ CFU to $10^{12}$ CFU, $10^8$ CFU to $10^{12}$ CFU, $10^5$ CFU to $10^{11}$ CFU, $10^6$ CFU to $10^{11}$ CFU, $10^7$ CFU to $10^{11}$ CFU, $10^8$ CFU to $10^{11}$ CFU, $10^5$ CFU to $10^{10}$ CFU, $10^6$ CFU to $10^{10}$ CFU, $10^7$ CFU to $10^{10}$ CFU, $10^8$ CFU to $10^{10}$ CFU, $10^5$ CFU to $10^9$ CFU, $10^6$ CFU to $10^9$ CFU, $10^7$ CFU to $10^9$ CFU, $10^5$ CFU to $10^8$ CFU, or $10^6$ CFU to $10^8$ CFU per unit dosage form.

The composition provided herein preferably contains *Lactobacillus plantarum* PDG8 bacteria or culture thereof in an amount sufficient to colonize the intestine of a subject when administered to the subject.

In certain embodiments, the present disclosure provides a pharmaceutical composition comprising isolated *Lactobacillus plantarum* PDG8 bacteria and a pharmaceutically acceptable excipient.

A pharmaceutically acceptable excipient includes pharmaceutically acceptable cryoprotectants, bulking agents, fillers, diluents, anti-adherents, binders, coatings, disintegrants flavoring agents, glidants, lubricants, preservatives, sorbents, sweeteners, and vehicles or carriers.

In certain embodiments, the pharmaceutical composition includes at least one cryoprotectant selected from the group consisting of glycerol, trehalose, maltodextrin, skim milk powder, and starch. The cryoprotectant of the present disclosure may be contained in an amount of 0.01% to 20% by weight or 0.01% to 10% by weight based on the total weight of the composition. Specifically, based on the total weight of the composition, the glycerol may be contained in an amount of 5% to 20% by weight, the trehalose may be contained in an amount of 2% to 10% by weight, the maltodextrin may be contained in an amount of 2% to 10% by weight, the skim milk powder may be contained in an amount of 0.5% to 2% by weight, and the starch may be contained in an amount of 0.1% to 1% by weight in the composition.

In certain embodiments, the excipient may include at least one or any combination of diluent (Tris, citrate, acetate or phosphate buffers) having various pH values and ionic strengths, solubilizer such as Tween® or polysorbate, carriers such as human serum albumin or gelatin, preservatives such as thimerosal, parabens, benzylalconium chloride or benzyl alcohol, antioxidants such as ascorbic acid or sodium metabisulfite, and other components such as lysine, glycine, glucose, dextrin, skim milk, mannitol or succinylated β-lactoglobulin. In addition, the excipient may be contained in an amount of 50% to 95% by weight, 75% to 95% by weight or 85% to 95% by weight based on the total weight of the composition.

Selection of a particular pharmaceutical composition will depend upon a number of factors, including the condition being treated, the route of administration and the pharmacokinetic parameters desired. A more extensive survey of components suitable for pharmaceutical compositions is found in Remington's Pharmaceutical Sciences, 18th ed. A. R. Gennaro, ed. Mack, Easton, Pa. (1980).

The route of administration of a pharmaceutical composition eventually chosen will depend upon a number of factors and can be ascertained by one skilled in the art. In certain embodiments, the compositions can be further formulated using pharmaceutically acceptable carriers well known in the art in dosages suitable for oral, nasogastric, or rectal administration. Such carriers enable the pharmaceutical compositions to be formulated as tablets, pills, capsules, liquids, gels, syrups, slurries, suspensions, enema formulations, and the like, for oral, rectal or nasogastric administration to a patient to be treated. Formulations can include, for example, polyethylene glycol, cocoa butter, glycerol and the like.

In some embodiments, the pharmaceutical composition may further include one or more additional therapeutic agents, such as anti-atherosclerosis agents.

The pharmaceutical composition can be administered in any sterile, biocompatible pharmaceutical carrier, including saline, buffered saline, dextrose, and water.

In certain embodiments, the present disclosure provides a nutraceutical composition comprising isolated *Lactobacillus plantarum* PDG8 bacteria or a culture thereof as an active ingredient. A "nutraceutical composition" refers to a food product or a food supplement capable of providing not only a nutritional effect and/or a taste satisfaction, but is also capable of delivering a therapeutic (or other beneficial) effect to a subject who consumes the composition. The nutraceutical composition may be in form of a probiotic composition, synbiotic composition, functional food, food supplement, or food product, including beverage.

The content of *Lactobacillus plantarum* PDG8 or cultures thereof in the nutraceutical composition may be based on the age or weight of the subject, desired effects, etc., and may be, for example, used in an amount of 0.0001% to 1% of the weight of the subject, such as 0.0001% to 0.001%, 0.0001% to 0.01%, 0.0001% to 0.1%, 0.001% to 0.01%, 0.001% to 0.1%, 0.01% to 0.10%, 0.010% to 10%, or 0.1 to 10% of the weight of the subject.

A nutraceutical composition of the present disclosure may further include a mixture of one or more of an organic acid such as citric acid, fumaric acid, adipic acid, lactic acid, etc.; a phosphate such as potassium phosphate, sodium phosphate, polyphosphate, etc.; or a natural antioxidant such as polyphenol, catechin, tocopherol, vitamin C, green tea extract, chitosan, tannic acid, etc.

In certain embodiments, isolated *Lactobacillus plantarum* PDG8, its culture, or a composition thereof may be used as a probiotic or probiotic composition. As used herein, the term "probiotics" refers to live bacteria that enter the body and provide a healthy benefit, such as improving the microbial balance of the body via, for example, ecological interactions with the resident flora in the digestive tract and/or reducing or eliminating symptoms or severity of a disorder (e.g., atherosclerosis) via, for example, influencing the host physiology and immune system in a positive manner.

The probiotic composition provided herein may further comprise one or more other probiotics, such as other *Lactobacillus*, *Bifidobacterium* and *Enterococcus* in the form of fermented milk, granules, powder, etc.

In certain embodiments, the present disclosure provides a symbiotic composition comprising isolated *Lactobacillus plantarum* PDG8 or a culture thereof and one or more prebiotics. A "prebiotic" refers to a substance having a beneficial effect on a probiotic, such as food for *Lactobacillus plantarum* PDG8. Exemplary prebiotics include inulin, pectin and resistant starches.

In certain embodiments, the present disclosure provides a food supplement comprising isolated *Lactobacillus plantarum* PDG8 or a culture thereof and one or more prebiotics. As used herein, a "food supplement," "supplement composition," or "dietary supplement" refers to a composition that contains a dietary ingredient (e.g., isolated *Lactobacillus plantarum* PDG8 or a culture thereof) intended to add nutritional value or health benefits to supplement the diet. A food supplement may be added to a food, but that is not itself a food or intended to be a food, or that may be ingested independently of a food. The food supplement disclosed herein may comprise, in addition to isolated *Lactobacillus plantarum* PDG8 or a culture thereof, one or more dietary ingredients such as a vitamin, a mineral, a herb or other botanical, and an amino acid.

A food supplement of the present disclosure may be an immediate-release or sustained-release formulation, and may further include a carrier, such as an edible carrier. The edible carrier may include corn starch, lactose, sucrose, or propylene glycol. A solid carrier may be used for tablets, powders, troches, etc., and a liquid carrier may include syrups, liquid suspensions, emulsions, solutions, etc. Further, the food supplement may include a preservative, a lubricant, a solution accelerator, or a stabilizer.

The disclosure further provides a functional food that contains *Lactobacillus plantarum* PDG8 or a culture thereof. As used herein, the term "functional food" refers to a human food that has a beneficial effect (e.g., medical or physiological benefit other than a purely nutritional effect) in addition to providing nutrition.

In certain embodiments, the present disclosure provides a food product comprising isolated *Lactobacillus plantarum* PDG8 or a culture thereof and one or more prebiotics. A "food product" means a product or composition that is intended for consumption by a human or a non-human animal. Such food products include any food, feed, snack, food supplement, liquid, beverage, treat, toy (chewable and/or consumable toys), meal substitute or meal replacement.

In a functional food or a food product of the present disclosure, the *Lactobacillus plantarum* PDG8 or cultures thereof may be present in an amount of 0.0001% to 1% by weight, specifically 0.001% to 0.1% by weight, based on a raw material composition including the *Lactobacillus plantarum* PDG8. However, in the case of long-term administration, the amount may be less than the above-described range, such as 0.001% to 0.01% by weight based on a raw material composition including the *Lactobacillus plantarum* PDG8.

There is no particular limitation on the type of the food to which *Lactobacillus plantarum* PDG8 or cultures thereof may be included. Examples of foods to which *Lactobacillus plantarum* PDG8 or cultures thereof can be added include meats, sausages, breads, chocolates, candies, snacks, confectionaries, pizzas, instant noodles, other noodles, gums, dairy products including ice creams, yoghurt, curdled milk, and whole milk, various kinds of soup, beverages, teas, drinks, alcoholic drinks, vitamin complexes, etc., and all functional foods.

A beverage or drink comprising *Lactobacillus plantarum* PDG8 or cultures thereof may further contain various flavoring agents or natural carbohydrates, as in conventional drinks. The aforementioned natural carbohydrates may include monosaccharides such as glucose, fructose, etc.; disaccharides such as maltose, sucrose, etc.; polysaccharides such as dextrin, cyclodextrin, etc.; and sugar alcohols such as xylitol, sorbitol, erythritol, etc. Natural sweetening agents such as thaumatin, a *stevia* extract, etc.; and synthetic sweetening agents such as saccharin, aspartame, etc. may be used as the sweetening agent. A ratio of the additional components may be in a range of 0.01 to 0.04 parts by weight, specifically 0.02 to 0.03 parts by weight, based on 100 parts by weight of the *Lactobacillus plantarum* PDG8 or cultures thereof.

The present disclosure further includes a method of preparing a composition as described herein, which may include a step of mixing an additive with the *Lactobacillus plantarum* PDG8, a culture thereof, a concentrate thereof, or a dried form thereof. The additive may be the above-described excipient, such as a cryoprotectant, or a carrier.

The *Lactobacillus plantarum* PDG8 may be cultured by a conventional method for culturing *Lactobacillus* strains. As the medium, a natural medium or a synthetic medium may be used. As the carbon source of the medium, for example, glucose, sucrose, dextrin, glycerol, starch, etc. may be used. As the nitrogen source, peptone, meat extracts, yeast extracts, dried yeasts, soybean, ammonium salts, nitrate, and other organic or inorganic nitrogen-containing compounds may be used, but the nitrogen source is not limited thereto. As the inorganic salts included in the medium, magnesium, manganese, calcium, iron, potassium, etc. may be used, but the inorganic salts are not limited thereto. Amino acids, vitamins, nucleic acids, and related compounds may be added to the medium in addition to the carbon source, the nitrogen source, and the components of the inorganic salts. The *Lactobacillus plantarum* PDG8 may be cultured for 12 hours to 4 days in a temperature range of 20° C. to 40° C.

Specifically, the culture broth of the *Lactobacillus plantarum* PDG8 may be a crude culture broth containing cells, and may also be cells from which a culture supernatant is removed, or concentrated cells. The composition of the culture broth may additionally contain not only components required for conventional culture of *Lactobacillus*, but also components that act synergistically to the growth of *Lactobacillus*, and the compositions thereof may be readily selected by those skilled in the art.

Methods of Treatment Using *Lactobacillus plantarum* PDG8

In another aspect, the present disclosure provides a method for treating a cardiovascular disease (e.g., atherosclerosis) comprising administering to a subject in need thereof a therapeutically effective amount of the isolated *Lactobacillus plantarum* PDG8 strain or a composition (e.g., a pharmaceutical composition) comprising the isolated *Lactobacillus plantarum* PDG8 strain or a culture thereof provided herein.

In related aspects, the present disclosure provides the isolated *Lactobacillus plantarum* PDG8 strain or a composition (e.g., a pharmaceutical composition) comprising the isolated *Lactobacillus plantarum* PDG8 strain or a culture thereof as described above for use in a method of treating the human or animal body by therapy, such as in a method for treating a cardiovascular disease (e.g., atherosclerosis).

Cardiovascular diseases (heart and blood vessel diseases) that may be treated by administering *Lactobacillus plantarum* PDG8 or a composition thereof include but are not limited to atherosclerosis, aorta disease, coronary artery disease, peripheral arterial disease, and rheumatic heart disease.

As used herein, "atherosclerosis" refers to an arterial disease characterized by the formation of fatty deposits, called "atherosclerotic plaques" on artery walls. Atherosclerosis, including the number and size of plaques, may be detected by imaging, but often has no symptoms until plaques are sufficiently large to impede blood flow. At that time, depending on the location and severity of the plaques, blood clots, carotid artery disease, chronic kidney disease, coronary artery disease, heart attack, peripheral artery disease, stroke, or other cardiovascular-related incidents may occur.

Atherosclerosis is characterized by endothelial dysfunction, large accumulation of low density lipoprotein (LDL), endothelial space necrosis debris and the presence of immune cells. The pathogenesis is complex and may be related to the injury of endothelial cells caused by harmful external stimuli. If the concentration of LDL in the blood is too high, it may be deposited in the endothelial space. After oxidative modification, the LDL becomes oxLDL and activates endothelial cells. The activated endothelial cells start to secrete leukocyte adhesion molecules to capture monocytes in the blood and trigger a series of the immune response, including the maturation of monocytes into macrophages, and then the scavenger receptor on the surface of macrophages recognizes oxLDL and activates the NF-κB signaling pathway, which enhances the release of pro-inflammatory factors such as IL-1β and TNF-α. Meanwhile, this process promotes the further differentiation of macro-phages into foam cells, and finally forms an atherosclerotic plaque (Herrero-Fernandez, B., et al. (2019). "Immunobiol-ogy of Atherosclerosis: A Complex Net of Interactions." *Int J Mol Sci* 20(21).)

This pathological process also develops with the migra-tion of smooth muscle cells from the arterial media to the intima, an increase in the synthesis of extracellular matrix macromolecules such as collagen, elastin, and proteoglycan, and an increase in a fibrous cap covering the necrotic core. (Libby, P., et al. (2011). "Progress and challenges in trans-lating the biology of atherosclerosis." *Nature* 473(7347): 317-325.) In addition, the complications of atherosclerosis also seriously endanger human health. Pro-inflammatory cytokines stimulate the production of connective tissue enzymes while accumulating in the plaques, causing the plaques to rupture, thereby triggering acute cardiovascular diseases.

An "individual," "subject," or "patient" herein is a ver-tebrate, such as a human or non-human animal, for example, a mammal. Mammals include, but are not limited to, humans, non-primates, farm animals, sport animals, rodents and pets. Examples of non-human animal subjects include rodents such as mice, rats, hamsters, and guinea pigs; rabbits; dogs; cats; sheep; pigs; goats; cattle; horses; and non-human primates such as apes and monkeys.

A "therapeutically effective amount" of a substance as used herein is that amount sufficient to effect beneficial or desired results, including clinical results, and, as such, an "effective amount" depends upon the context in which it is being applied. In some embodiments, in the context of administering a composition to treat a cardiovascular dis-ease, the severity, frequency, or duration of at least one symptom of the cardiovascular disease may be reduced when a therapeutically effective amount is administered.

As used herein, and as understood in the art, "treatment" or "treating" is an approach for obtaining beneficial or desired results, including clinical results. For purposes of this subject matter, beneficial or desired clinical results include, but are not limited to, prevention, alleviation or amelioration of one or more symptoms, diminishment of extent of disease, stabilized (i.e., not worsening) state of disease, prevention of disease, delay or slowing of disease progression, reduced risk of recurrence of disease, and/or amelioration or palliation of the disease state.

*Lactobacillus plantarum* PDG8, a composition, or a food or supplement composition as described herein may be administered to a subject. In particular, a therapeutically effective amount of the *Lactobacillus plantarum* PDG8, a composition, or a food or supplement composition as described herein may be administered to a subject having a cardiovascular disease (e.g., atherosclerosis). The therapeu-tically effective amount of the composition, or food or supplement composition may depend on many factors, such as the age, weight, and severity of the cardiovascular disease in the subject, the length of treatment, other therapeutics concurrently administered to the subject, and gastrointesti-nal conditions of the subject.

In some embodiments, the *Lactobacillus plantarum* PDG8, a composition, or a food or supplement composition may be administered in an amount sufficient for detectable colonization of the intestine of the subject with *Lactobacil-lus plantarum* PDG8. Colonization may be tested a set period of time after administration of the *Lactobacillus plantarum* PDG8 or a composition comprising the *Lacto-*

*bacillus plantarum* PDG8 bacteria or a culture thereof, such as after one day, one week, two weeks, three weeks, or one month.

In specific embodiments, *Lactobacillus plantarum* PDG8 or a composition thereof may be administered with another therapeutic for treating a cardiovascular disease (e.g., ath-erosclerosis). The administration of the other therapeutic may be at the same time as, prior to, or subsequent to the administration of *Lactobacillus plantarum* PDG8 or a com-position thereof. Dosage of the other therapeutic may be reduced over time as the *Lactobacillus plantarum* PDG8 colonizes the intestine of the subject.

The *Lactobacillus plantarum* PDG8 or a composition thereof may be administered to a subject once, or multiple times, such as daily, weekly, biweekly, every three weeks, monthly, every two months, every six months, every year, or whenever the *Lactobacillus plantarum* PDG8 is not detect-able in the intestine of the subject.

The subject may be a human, but, in some embodiments, it may be another animal susceptible to a cardiovascular disease (e.g., atherosclerosis), such as a dog, cat, cow, goat, or horse.

The *Lactobacillus plantarum* PDG8 or a composition thereof may be administered to a subject orally, nasogas-tricly or rectally. Preferably, the administration is oral administration.

In some embodiments, the *Lactobacillus plantarum* PDG8 or a composition thereof may be administered so that the *Lactobacillus plantarum* PDG8 dose is an amount of $10^5$ CFU/day or more, $10^6$ CFU/day or more, $10^7$ CFU/day or more, $10^8$ CFU/day or more, $10^9$ CFU/day or more, $10^{10}$ CFU/day or more, $10^{11}$ CFU/day or more, $10^{12}$ CFU/day or more, or $10^{13}$ CFU/day or more, or in a range between any of these amounts (e.g., $10^5$ CFU to $10^{13}$ CFU per day).

The *Lactobacillus plantarum* PDG8 or a composition thereof may be administered repeatedly until at least one symptom of a cardiovascular disease (e.g., atherosclerosis) in the subject improves.

In certain embodiments, the administration of *Lactoba-cillus plantarum* PDG8 or a composition thereof to a subject may reduce the formation of atherosclerotic plaques, body fat inflammation, and/or blood lipid. Specifically, the admin-istration of *Lactobacillus plantarum* PDG8 or a composition thereof may result in one or more of the following: reducing accumulation of fat (e.g., abdominal fat), reducing forma-tion, number and/or sizes of atherosclerotic plaques, reduc-ing amount of blood lipid (e.g., total cholesterol, triglyceride and low-density lipoprotein cholesterol), reducing expres-sion of pro-inflammatory factors (e.g., TNF-α, IL-6), and improving the integrity of the intestinal barrier. Methods for measuring accumulation of fat formation, number and/or sizes of atherosclerotic plaques, amount of blood lipid (e.g., total cholesterol, triglyceride and low-density lipoprotein cholesterol), expression levels of pro-inflammatory factors (e.g., TNF-α, IL-6), and the integrity of the intestinal barrier are known, examples of which are described in Examples 3-7.

EXAMPLES

The presently disclosed subject matter will be better understood by reference to the following Examples, which are provided as exemplary of the invention, and not by way of limitation.

Example 1: Identification of *Lactobacillus plantarum* PDG8

The bacterial strain from home-made fermented veg-etables was separated and purified to form isolated *Lacto-*

13

14

*bacillus plantarum* PDG8. Specifically, the slurry juice was diluted to $10^{-3}$ or $10^{-4}$, and inoculated in modified MRS medium, then cultured anaerobically at 30° C. for 48 h. Colonies were counted, then picked. Each colony picked was inoculated in MRS liquid medium and cultured in anaerobic conditions for 48 h. Strains were purified by repeated streaking. The isolated and purified strains were cultured anaerobically at 30° C. for 48 h, and the cells were collected by centrifugation.

A Biospin Bacteria Genomic DNA Extraction Kit was used to extract DNA from the isolated bacteria. Purity and concentration of DNA was determined. Covaris M220 was used to fragment genomic DNA, and an Invitrogen Qubit 4.0 fluorescence quantifier was used for concentration quantification. A KAPA Hyper Prep Kit was used for library construction and the Illumina NovaSeq was used for sequencing. 42 contigs (SEQ ID NOS: 1-42) were obtained.

The original sequences obtained were classified and the genome was assembled and compared with the 63,400 assembled gene sequences of NCBI by MASH (version: 2.2). Identification was based on mash distance information. Similarity to *Lactobacillus plantarum* was 99.68%. Therefore, the newly isolated strain was named *Lactobacillus plantarum* PDG8.

Example 2: Establishment of ApoE$^{-/-}$ Mouse Atherosclerosis Model

As shown in FIG. 1, 6-week-old ApoE$^{-/-}$ male mice were prepared for one week (12/12 light and dark alternate, free drinking and eating) and then randomly divided into 3 groups: a control group, a model group, and a probiotics group. 4 ApoE$^{-/-}$ mice in the control group ("Chow") received a normal diet and gavage PBS. 6 ApoE$^{-/-}$ mice in the model group ("Model") received a high-fat diet and gavage PBS. 6 ApoE$^{-/-}$ mice in the probiotic group ("G8") were received a high-fat diet and gavage with *Lactobacillus plantarum* PDG8 at 1×$10^8$ CFU/day/mouse. The test was conducted for 10 weeks, and results were obtained as set forth in Examples 3-7.

Figure 2:
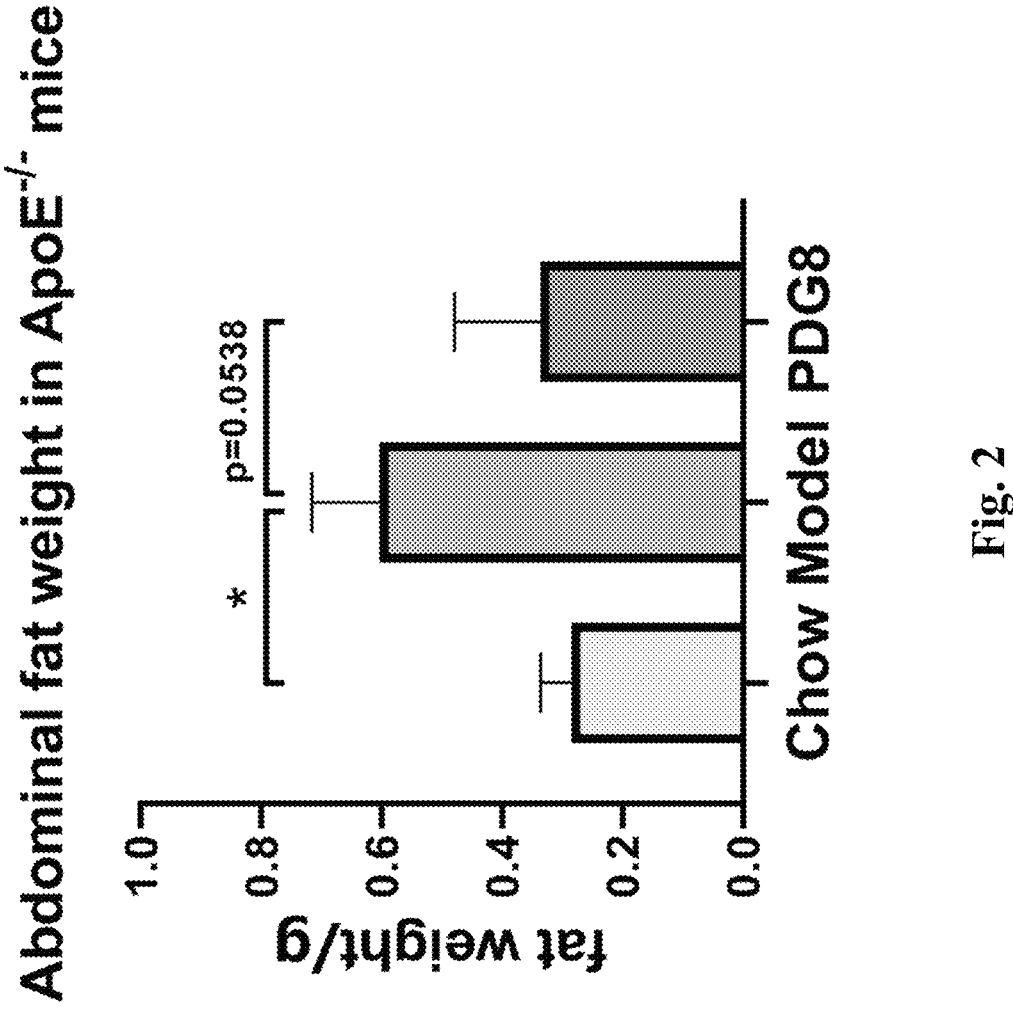
FIG. 2 shows the result of the effect of *Lactobacillus plantarum* PDG8 on the weight of abdominal fat in $ApoE^{-/-}$ male mice.

Example 3: *Lactobacillus plantarum* PDG8 Reduces Abdominal Fat Weight in ApoE$^{-/-}$ Male Mice At the end of the 10 week period and after the other experiments were completed, the animals were sacrificed and fixed on a dissecting board. The abdominal cavity was opened to separate white adipose tissue, which was then weighed. As shown in FIG. 2, the weight of abdominal fat accumulation in the model group was significantly higher than that of the control group ($p<0.05$). Compared with the model group, the weight of abdominal fat decreased after 10 weeks of treatment with *Lactobacillus plantarum* PDG8 ($p=0.0538$). These results demonstrate that the high-fat diet caused the weight of fat in the mice to increase, but *Lactobacillus plantarum* PDG8 reduced the weight of fat increase to a level similar to that in the mice not fed with a high-fat diet.

Example 4: *Lactobacillus plantarum* PDG8 Reduces Atherosclerosis in ApoE$^{-/-}$ Male Mice In the scarified animals, the front chest skin was cut open and the sternum and the entire rib cage removed to expose the entire abdominal cavity and thoracic cavity. 10 ml of 4° C. pre-cooled PBS solution (autoclaved) was placed in a 50 mL infusion needle/syringe. A small opening was cut in the right atrial appendage, the left ventricle (apex) was pierced with the infusion needle. The PBS was injected slowly and evenly until the liquid flowing out was clear. After the perfusion, the lungs were cut out from the pedicle leaf by leaf, leaving only the heart, thymus, and aorta in the thoracic cavity. The entire aortic tree was removed from the heart and the blood vessels were cut open and fixed in 4% paraformaldehyde. After fixing for more than 24 hours, oil red O staining was performed.

Figure 3A:
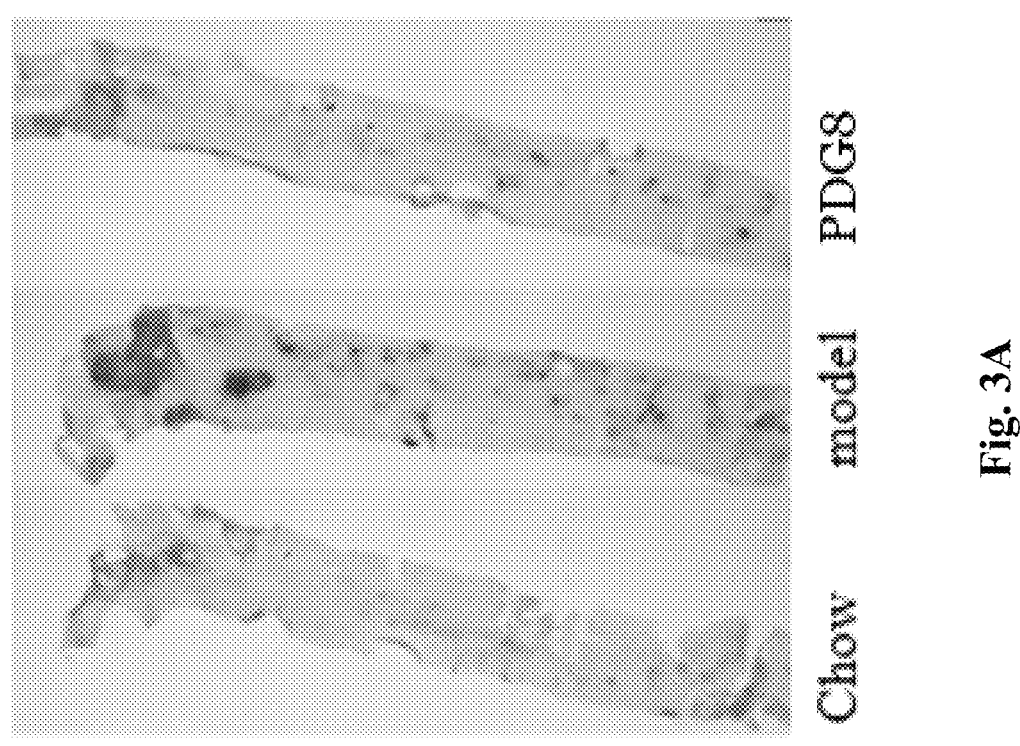
FIGS. 3A and 3B show the effects of *Lactobacillus plantarum* PDG8 on the formation of atherosclerotic lesions in $ApoE^{-/-}$ male mice.

After staining, pictures were taken with a general microscope, and image J software was used to measure the area of aortic lesions. Results are shown in FIG. 3A. Compared with the model group, *Lactobacillus plantarum* PDG8 significantly reduced the formation of atherosclerotic plaques.

Figure 3B:
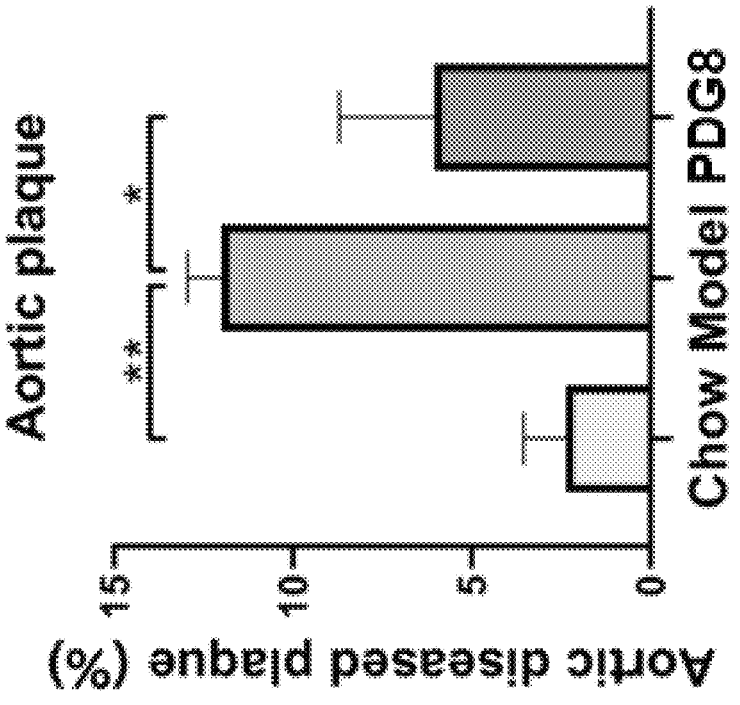

As shown in FIG. 3B, compared with the control group, the aortic lesions in the model group increased significantly ($p<0.01$). Although the *Lactobacillus plantarum* PDG8-treated group did not have aortic lesions at as low a level as the control group, it still exhibited a significantly reduction compared with the model group ($p<0.05$). This demonstrates that *Lactobacillus plantarum* PDG8 could treat aortic diseases such as atherosclerosis induced by high-fat diet.

Figure 4A:
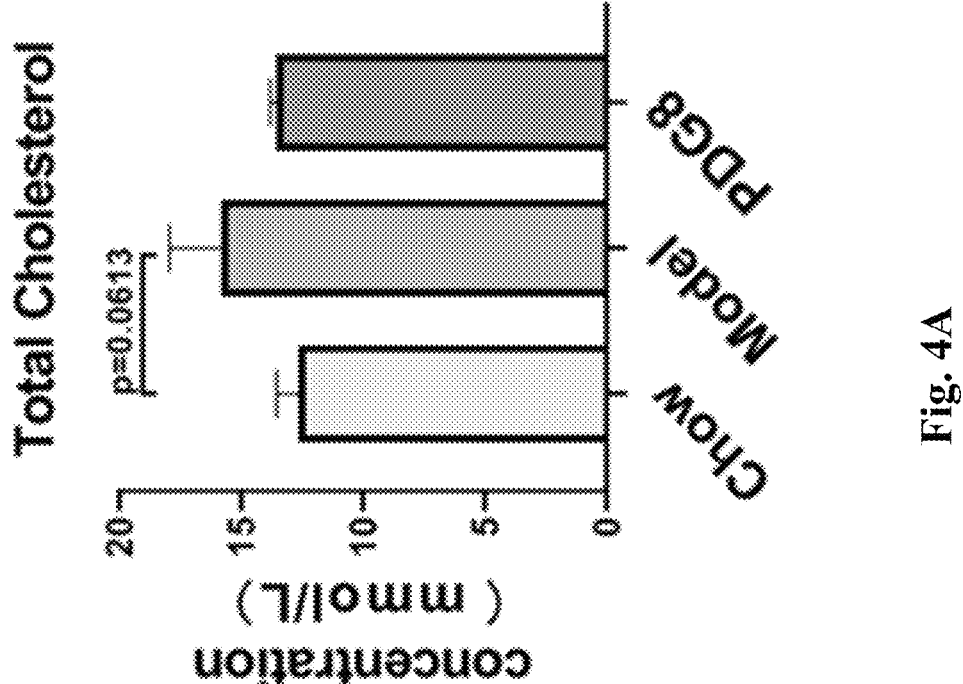
FIGS. 4A-4C show the effect of *Lactobacillus plantarum* PDG8 on the blood lipid levels of the aorta of $ApoE^{-/-}$ male mice.
Figure 4B:
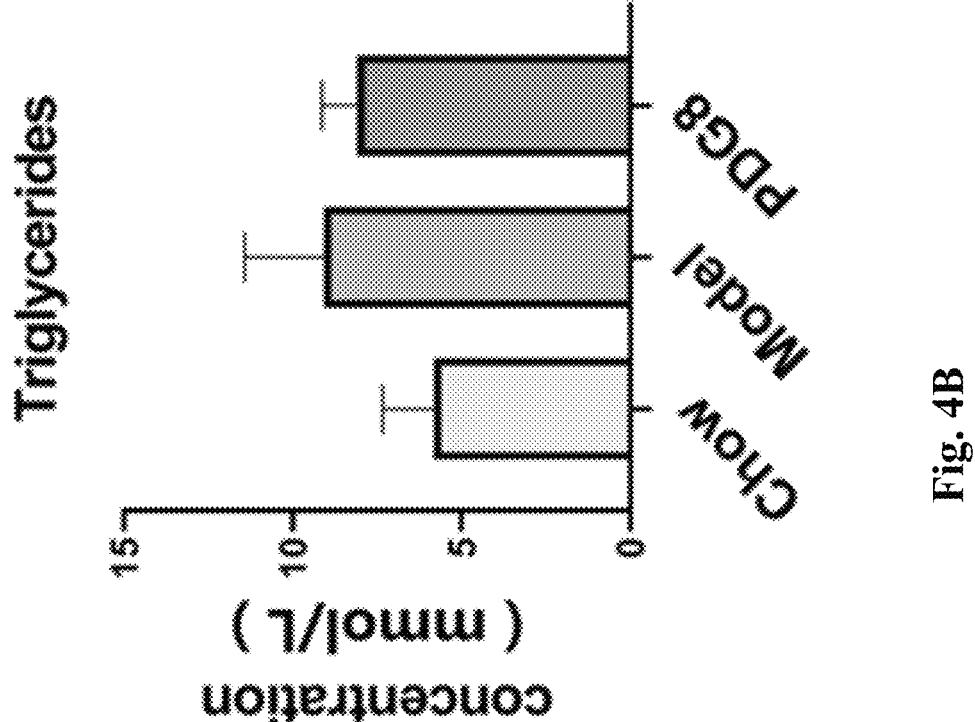
Figure 4C:
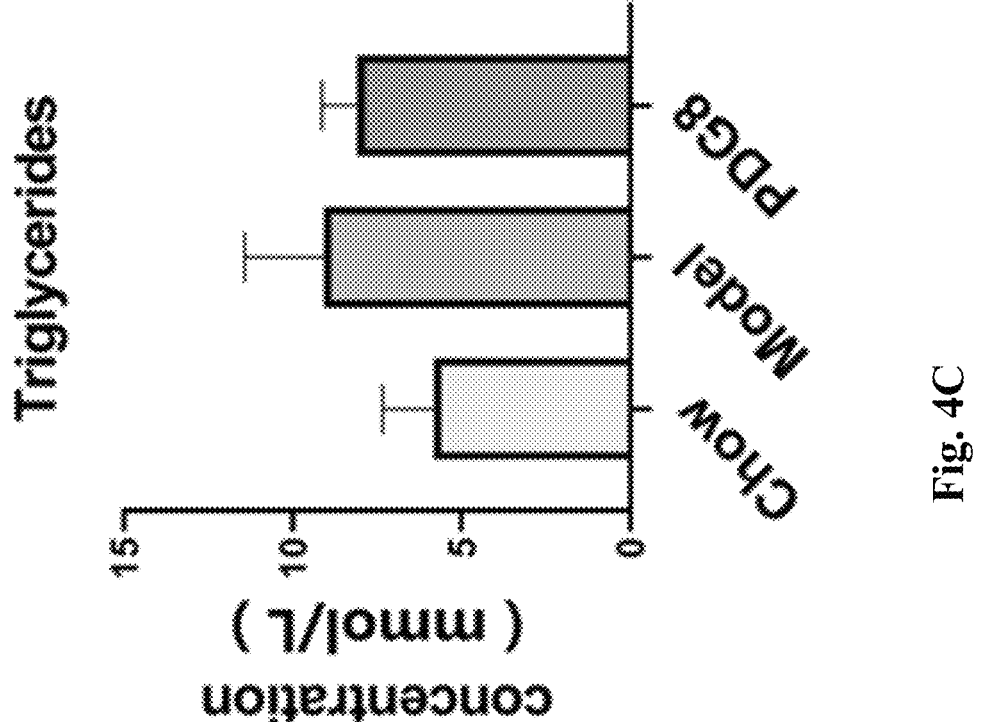

Example 5: Effect of *Lactobacillus plantarum* PDG8 on Blood Lipid Levels in ApoE$^{-/-}$ Male Mice Mouse orbital whole blood was collected, and the content of total cholesterol (FIG. 4A), triglyceride (FIG. 4B) and low-density lipoprotein cholesterol (FIG. 4C) in the serum were measured. As shown in FIGS. 4A-4C, the high-fat diet increased the blood lipid levels of mice in the model group, but after 10 weeks of treatment with *Lactobacillus plantarum* PDG8, all levels of the tested types of blood lipids dropped. This indicates that *Lactobacillus plantarum* PDG8 improved the imbalance of blood lipid levels induced by high-fat diet.

Figure 5A:
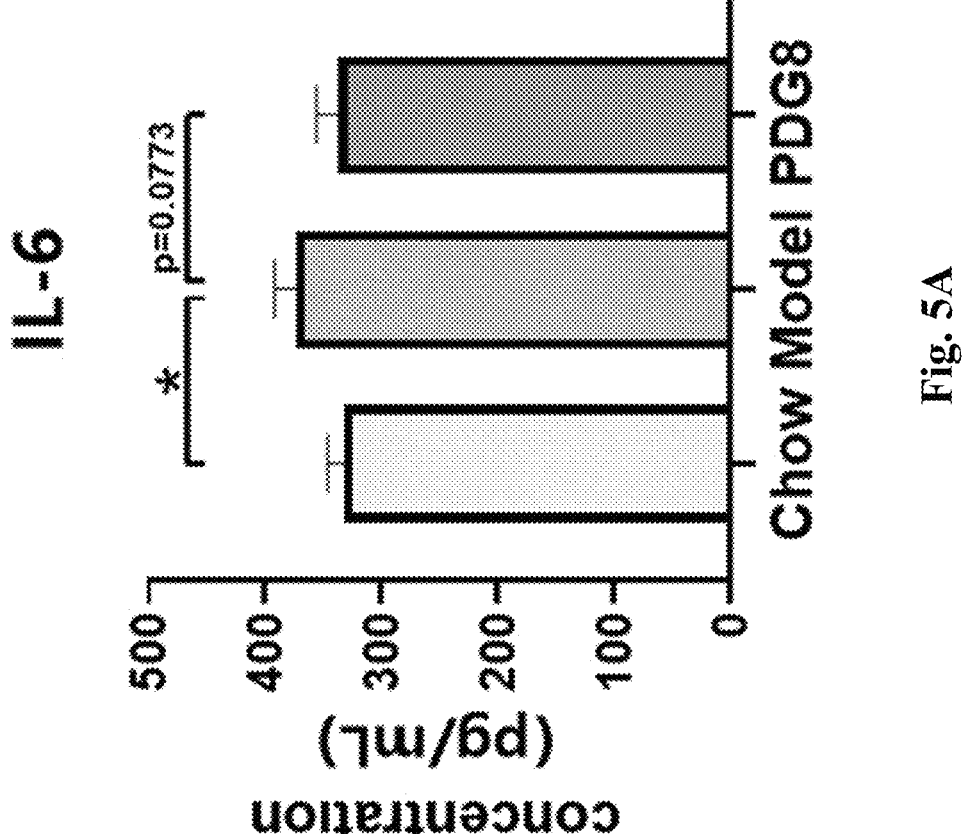
FIGS. 5A and 5B show the results of the effect of *Lactobacillus plantarum* PDG8 on the levels of inflammatory cytokines in $ApoE^{-/-}$ male mice.
Figure 5B:
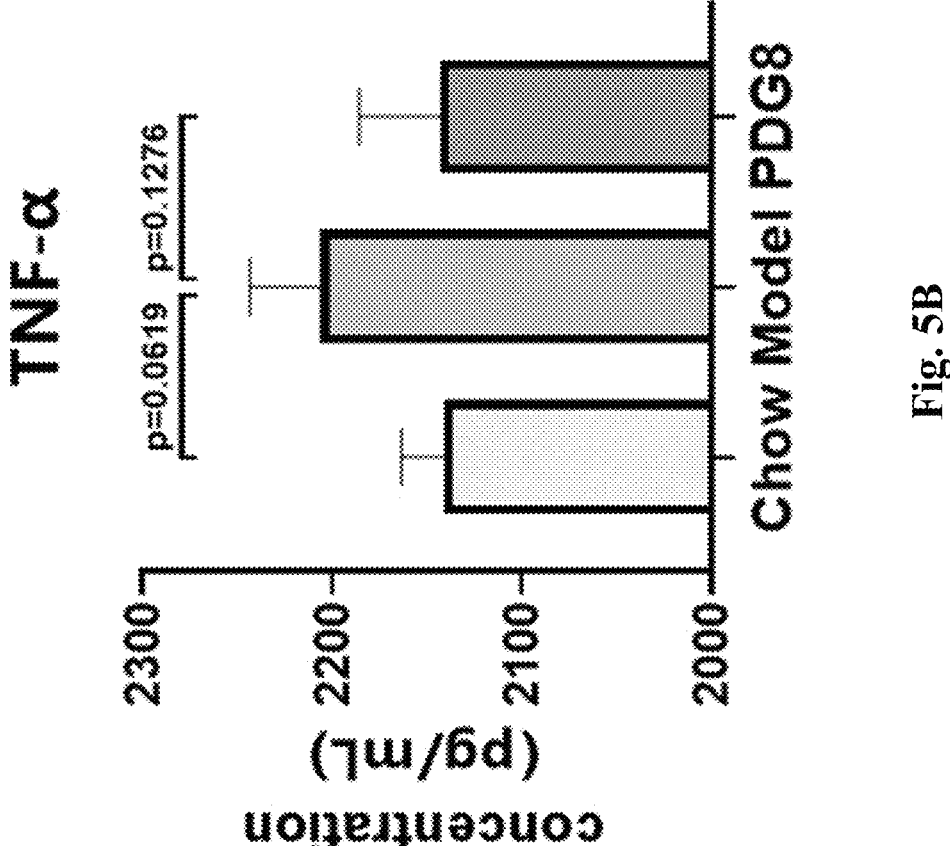

Example 6: Effect of *Lactobacillus plantarum* PDG8 on Inflammatory Factor Levels in ApoE$^{-/-}$ Male Mice Orbital whole blood was collected, and the expression levels of TNF-α and IL-6 in serum were measured. As shown in FIGS. 5A and 5B, a high-fat diet increased the levels of the inflammatory factors TL-6 (FIG. 5A) and TNF-α (FIG. 5B) in the model group. After 10 weeks of treatment with *Lactobacillus plantarum* PDG8, the levels of both inflammatory factors dropped. This indicates that *Lactobacillus plantarum* PDG8 alleviated the inflammation caused by atherosclerosis in mice.

Figure 6:
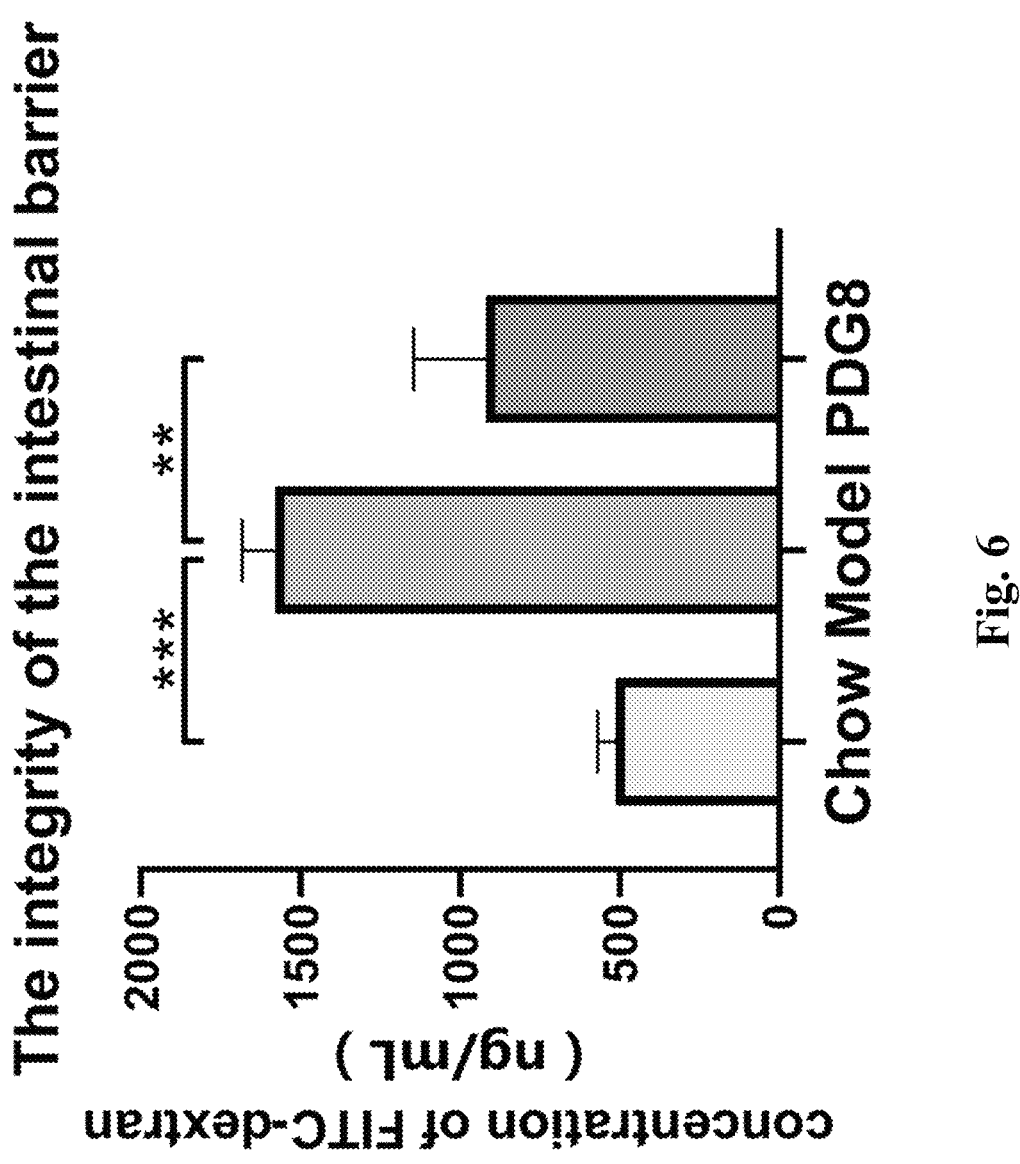
FIG. 6 shows the effect of *Lactobacillus plantarum* on the integrity of the intestinal barrier of $ApoE^{-/-}$ mice.

Example 7: Effect of *Lactobacillus plantarum* PDG8 on Integrity of the Intestinal Barrier in ApoE$^{-/-}$ Male Mice Four hours before the mice were sacrificed, the mice were given intragastrically a dose of 0.6 mg/g FITC-dextran. After the mice were sacrificed, a serum sample was obtained and the FITC content in the serum was measured with a fluorescence spectrophotometer. The results are shown in FIG. 6. Compared with the control group, the concentration of dextran in the serum of the model group increased significantly ($p<0.001$), while prior treatment with *Lactobacillus plantarum* PDG8 significantly reduced the concentration of dextran in the serum of mice. ($P<0.01$). This indicates that *Lactobacillus plantarum* PDG8 reduced the intestinal barrier damage induced by a high-fat diet.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

SEQUENCE LISTING

The patent contains a lengthy sequence listing. A copy of the sequence listing is available in electronic form from the USPTO web site (https://seqdata.uspto.gov/docdetail?docId=US12594311B2). An electronic copy of the sequence listing will also be available from the USPTO upon request and payment of the fee set forth in 37 CFR 1.19(b)(3).

The invention claimed is:

1. A non-naturally-occurring composition comprising an isolated *Lactobacillus plantarum* PDG8 strain deposited at Guangdong Microbial Culture Collection Center (GDMCC) under the accession number 62261 and an excipient, wherein the strain is present in an amount ranging from $10^3$ to $10^8$ CFU/mL or $10^5$ to $10^{13}$ CFU/g of the composition.

2. The composition of claim 1 comprising the *Lactobacillus plantarum* PDG8 strain in an amount ranging from $10^3$ to $10^8$ CFU/mL.

3. The composition of claim 1, wherein the composition is a pharmaceutical composition.

4. The composition of claim 3, wherein the composition is formulated for oral, nasogastric, or rectal administration.

5. The composition of claim 1, wherein the composition is a nutraceutical composition.

6. The composition of claim 5, wherein the composition is in the form of a probiotic composition, symbiotic composition, food supplement, functional food, food product, or beverage.

7. The composition of claim 1, wherein the composition is a liquid.

8. The composition of claim 1, wherein the composition is dried.

9. The composition of claim 8, wherein the composition is lyophilized or freeze-dried.

10. The composition of claim 1 comprising the *Lactobacillus plantarum* PDG8 strain in an amount sufficient to colonize the intestine of a subject when administered to the subject.

11. The composition of claim 1 comprising the *Lactobacillus plantarum* PDG8 strain in an amount ranging from $10^5$ to $10^{13}$ CFU/g.

12. The composition of claim 1, wherein the composition is in unit dosage form.

13. The composition of claim 12, wherein the *Lactobacillus plantarum* PDG8 strain is present in the composition in an amount between $10^5$ to $10^{13}$ CFU per unit dose.

14. A method of treating atherosclerosis comprising administering orally to a mammalian subject in need thereof a therapeutically effective amount of a composition comprising an isolated *Lactobacillus plantarum* PDG8 strain deposited at Guangdong Microbial Culture Collection Center (GDMCC) under the accession number 62261 and a pharmaceutically acceptable excipient.

15. The method of claim 14 comprising administering the therapeutically effective amount in multiple doses.

16. The method of claim 15 comprising administering the therapeutically effective amount daily for at least a week.

17. The method of claim 14 comprising administering the therapeutically effective amount until the intestine of the subject is detectably colonized with the *Lactobacillus plantarum* PDG8 strain.

18. The method of claim 14, wherein the therapeutically effective amount is in a range of $10^5$ to $10^{13}$ CFU per day.

19. The method of claim 14, wherein the number or the areas of atherosclerotic plaques in the subject are reduced compared to a corresponding subject not fed with the composition.

20. The method of claim 14, wherein the expression level of a pro-inflammatory factor in the serum of the subject is reduced compared to a corresponding subject not fed with the composition, wherein the pro-inflammatory factor is IL-6 or TNF-alpha.

21. The method of claim 14, wherein the level of total cholesterol, triglyceride, or low-density cholesterol in the serum of the subject is reduced compared to a corresponding subject not fed with the composition.

22. The method of claim 14, wherein the amount of abdominal fat of the subject is reduced compared to a corresponding subject not fed with the composition.

* * * * *